United States Patent [19]

Ellwood et al.

[11] Patent Number: 4,696,900

[45] Date of Patent: Sep. 29, 1987

[54] PRODUCTION OF BACTERIAL POLYSACCHARIDES

[75] Inventors: Derek C. Ellwood, Winterbourne Stoke; Charles G. T. Evans; Richard G. Yeo, both of Salisbury, all of England

[73] Assignee: The Secretary of State for Defence in Her Majesty's Government of the United Kingdom of Great Britain and Northern Ireland, London, England

[21] Appl. No.: 617,743

[22] Filed: Jun. 6, 1984

Related U.S. Application Data

[63] Continuation-in-part of Ser. No. 097,449, Nov. 26, 1979, abandoned, which is a continuation-in-part of Ser. No. 766,037, Feb. 7, 1977, abandoned, which is a continuation-in-part of Ser. No. 739,145, Nov. 5, 1976, abandoned.

[30] Foreign Application Priority Data

Nov. 12, 1975 [GB] United Kingdom ............... 46784

[51] Int. Cl.$^4$ .................... C12P 19/06; C12R 1/64
[52] U.S. Cl. .................... 435/104; 435/813; 435/910
[58] Field of Search ............ 435/101, 102, 103, 104, 435/813, 910, 253

[56] References Cited

U.S. PATENT DOCUMENTS

| | | | |
|---|---|---|---|
| 2,822,319 | 2/1958 | Monod | 435/253 |
| 3,020,206 | 2/1962 | Patton et al. | 435/132 |
| 3,271,267 | 9/1966 | Weber | 435/104 |
| 3,281,329 | 10/1966 | Lipps | 435/104 |
| 3,328,262 | 6/1967 | Lindblom et al. | 435/3 |
| 3,391,060 | 7/1968 | McNeely | 435/104 |
| 3,391,061 | 7/1968 | McNeely | 435/104 |
| 3,455,786 | 7/1969 | Miescher | 435/104 |
| 3,485,719 | 12/1969 | Rogovin | 435/104 |
| 4,282,321 | 8/1981 | Wernau | 435/104 |
| 4,311,796 | 1/1982 | Weisrock | 435/104 |
| 4,394,447 | 7/1983 | Cadmus et al. | 435/104 |
| 4,400,467 | 8/1983 | Bauer et al. | 435/104 |
| 4,618,582 | 10/1986 | Kirchen et al. | 435/104 |

FOREIGN PATENT DOCUMENTS

| | | |
|---|---|---|
| 161467 | 11/1975 | Czechoslovakia . |
| 2251620 | 6/1975 | France . |
| 2331614 | 6/1977 | France . |
| 1512536 | 6/1978 | United Kingdom . |
| 1531644 | 11/1978 | United Kingdom . |

OTHER PUBLICATIONS

Silman et al., "Continuous Fermentation to Produce Xanthan Biopolymer: Laboratory Investigation", Biotech. & Bioeng. vol. XII, pp. 75-83 (1970).
Starr, "The Nutrition of Phytopathogenic Bacteria", J. Bacteriology, vol. 51, pp. 131-143, (1946).
Cadmus, et al., -Cereal Chem., 1966, 43, 658.
Bagley, M. O., Tappi, 1969, 52, 442.
A. Atkinson, et al., Biotech. Bioeng. 1975, 17, 1375.
D. C. Ellwood et al., Arch Oral Biol, 1974, 19, 659.
P. B. Riley et al., Continuous Culture of Microorganisms, Soc. Chem. Ind. Monograph No. 12, 1962, 127.
Silman et al., Continuous Fermentation to Produce Xanthan Biopolymer: Effect of Dilution Rate", Biotech. & Bioerg. vol. 14(1972) pp. 23-31.
Buchanan et al, Bergy's Manual of Determinative Bacteriology, 8th Ed., The Williams & Wilkes Co., Baltimore (1974) pp. 244-246.
Neussel and Tempest, "The Regulation of Carbohydrate Metabolism in Klebsiella aerogenes NCTC 418 Organisms, Growing in Chemostat Culture" Arch Microbiol., vol. 106 (1975) pp. 251-258.
Slodski and Cadmus, Adv. Appl. Microbiol. 1978, 23, 19 at p. 52, line 25.
P. N. Hobson, J. Gen Microbiol., 1965, 38, 167.
"The Adequacy of the Usual Determinative Tests for the Identification of Xanthomonos spp." New Zealand J. Sci., vol. 5 (1962) pp. 396-416.
Evans, Herbert et al., "Methods in Microbiology, vol. 2, pp. 310-313, Norris & Ribbons, Academic Press 1970.

Primary Examiner—Thomas G. Wiseman
Assistant Examiner—Elizabeth C. Weimar
Attorney, Agent, or Firm—Stevens, Davis, Miller & Mosher

[57] ABSTRACT

Polysaccharides are produced by single stage continuous culture of Xanthomonas bacteria, especially of the Xanthomonas campestris group in a chemically-defined culture medium. Cultures have been run for over 2,000 hours without reduction in the polysaccharide yield. The physical and chemical properties of the product can be controlled by selection of the growth limiting substrate (limiting nutrilite) in the culture medium to give a range of polysaccharides suitable for various applications.

23 Claims, No Drawings

PRODUCTION OF BACTERIAL POLYSACCHARIDES

This application is a continuation-in-part of application Ser. No. 097,449 filed Nov. 26, 1979, now abandoned itself a continuation-in-part of application Ser. No. 766,037 filed Feb. 7, 1977, now abandoned itself a continuation-in-part of application Ser. No. 739,145 filed Nov. 5, 1976 now abandoned.

BACKGROUND TO THE INVENTION

It is well known that certain bacteria of the genus Xanthomonas, notably the *Xanthomonas campestris* group, when cultured under suitable conditions are capable of producing hetero-polysaccharides, commonly termed "Xanthan gum", which are useful as thickeners and emulsifiers in a variety of applications including foodstuffs and drilling muds. In general the bacteria are grown in batch culture, typically for 48 to 72 hours, in conventional complex culture media containing nutrients such as corn starch (U.S. Pat. No. 3,455,786), soy peptone (U.S. Pat. Nos. 3,391,060 and 3,391,061) distillers solubles (French Pat. No. 2,251,620) or "Stimuflav" (U.S. Pat. No. 3,020,206).

U.S. Pat. No. 3,391,060 (McNeely) described the use of ammonium nitrate as a nitrogen source in the final culture medium, but observes that to build up the bacterial population to a satisfactory level a complex nitrogen source is essential in the seed cultures and may also be used in the final culture in addition to ammonium nitrate. Thus U.S. Pat. No. 3,391,060 employs a semi-, rather than a fully, defined culture medium containing the ammonium nitrate of the final fermentation medium and the complex nitrogen sources of the seed cultures. That this was the intention of the patentee is illustrated by a later publication (Industrial Gums, 2nd Edn, Academic Press, 1973 at p 488) in which McNeely states that an inorganic nitrogen source and a protein supplement are necessary for efficient polysaccharide production.

Similarly, Starr (J Bact., 1946, 51, 131), whilst reporting that certain strains of Xanthomonas will grow in a defined medium, concludes that the rate of bacterial growth is considerably faster in a complex medium. Furthermore, the authoritative Bergey's Manual of Determinative Bacteriology (8th Edn) states that the minimal growth requirements of Xanthomonas are complex. It should also be noted that Starr does not address the question of polysaccharide production. It is not enough that a Xanthomonas strain will grow in a particular medium, it must also efficiently produce polysaccharide in that medium.

Many applications of xanthan gum require large quantities of the material and therefore considerable attention has been given to the economics of its production.

Batch production of xanthan gum requires at least 48 to 72 hours to achieve maximum yield, whilst similar yields per unit volume of culture may be obtained in 12 to 50 hours by continuous methods. The desirability of producing xanthan gum by continuous method was therefore recognised at an early stage (U.S. Pat. No. 3,328,262, Lindblom and Patton). However successive attempts to produce an economically viable system (U.S. Pat. No. 3,485,719, Rogovin; Silman and Rogovin, Biotechnol. Bioeng, 1970, 12, 75 and 1972, 14, 23) were unsuccessful because the bacteria: (Xanthomonas), under the conditions employed, developed into strains that did not produce polysaccharide. (It should be noted that to compete with a batch system, a continuous culture should proceed for at least 10 turnovers of culture medium (culture turnover=Q=length of culture×dilution rate), and preferably for much longer than that).

It had long been known that only certain strains of Xanthomonas bacteria were capable of producing polysaccharide, the suitable strains normally being those which produce smooth globular colonies when plated onto nutrient agar containing glucose. Attempts to produce polysaccharide by the continuous culture of these "smooth strains" showed that, although cell growth proceeded as expected, polysaccharide yield fell to unacceptably low levels after a short time; this fall was attributed to the development, as the culture progressed, of non-polysaccharide producing Xanthomonas strains.

Thus Silman and Rogovin (supra) concluded that cultures could not be continued beyond 6.5 to 8.7 culture turnovers, whilst Rogovin (supra) noted that in his process (which was not truly continuous); "contamination" occurred after 6.5 culture turnovers.

Thus despite numerous attempts (see also U.S. Pat. No. 3,328,262 and U.S. Pat. No. 3,281,329 (Lipps)), no successful process for producing polysaccharides by a simple, single stage continuous culture of Xanthomonas bacteria has so far been described.

The present inventors have now found that by employing a different culture medium from that used by Silman, Rogovin, etc, Xanthomonas strain variability in continuous culture may be substantially reduced and fall-off in polysaccharide yield thereby substantially avoided.

The medium chosen by the present inventors is a chemically defined culture medium. This replaces the complex media favoured in the prior art processes. Surprisingly, and contrary to the teaching of Bergey and of McNeely the use of a chemically defined medium, as taught herein, adversely affects neither bacterial cell growth nor polysaccharide production.

SUMMARY OF THE INVENTION

Thus according to the present invention there is provided a process for the production of a polysaccharide by culturing polysaccharide producing bacteria of the genus Xanthomonas in continuous culture comprising:
  (a) introducing into a culture vessel a culture of polysaccharide producing bacteria of the genus Xanthomonas,
  (b) continuously supplying a culture medium, at a controlled rate, to the culture vessel.
  (c) maintaining conditions of aeration, pH and temperature within the culture vessel to promote the simultaneous growth of bacteria and production of polysaccharide, and
  (d) continuously withdrawing the resulting polysaccharide containing culture broth from the culture vessel at substantially the same rate as the culture medium is supplied to the culture vessel,
the said culture medium being a chemically defined culture medium consisting essentially of the following nutrient sources, a carbon source at a concentration of at least 10 gm liter$^{-1}$ (calculated as elemental carbon), a nitrogen source selected from an inorganic salt, an amino acid and an amino acid salt and sources of phosphorus, sulphur, magnesium, potassium and other essential elements in the form of inorganic salts;
the relative concentrations of the nutrient sources being known and the medium having a growth limiting substrate which is selected from the nitrogen, phosphorus, sulphur, magnesium and potassium source;
and the nutrient sources, the rate of supply of the culture medium to the culture vessel and the conditions within the culture vessel being selected such that the formation of non-polysaccharide producing strains of Xanthomonas is substantially reduced and thereby a fall-off in polysaccharide yield is substantially avoided.

DETAILED DESCRIPTION OF THE INVENTION

The invention is especially applicable to polysaccharide-producing Xanthomonas bacteria falling within the "campestris group" as defined by "Bergey's Manual of Determinative Bacteriology", 8th Edition. Bacteria of the species *Xanthomonas juglandis* have been found suitable, for example the known strain of *Xanthomonas juglandis* deposited with the International Collection of Phytopathogenic Bacteria, USA, under the reference number ICPB XJ107 and publicly available (subject to national plant health regulations). Other strains of *Xanthomonas juglandis* include selected polysaccharide producing colonies of those deposited with the National Collection of Plant Pathogenic Bacteria, England, under Nos. NCPPB 362, 411, 412, 413, 414, 415, 1447 and 1659 and with the American Type Culture Collection under No ATCC 11329. Other species such as *Xanthomonas campestris* itself, for example the strain ATCC 13951, may also be grown to produce polysaccharide in a single stage continuous culture under the conditions of the invention.

Xanthomonas bacteria can be recognised, according to Bergey's Manual of Determinative Bacteriology, as follows:

"Cells single, straight rods. Dimensions 0.2–0.8 by 0.6–2.0 μm, usually ca. 0.4–1.0 μm. Motile be means of a polar flagellum. Do not produce sheaths. No resting stages known. Gram-negative.

Growth on agar media usually yellow.

Chemoorganotrophs, Metabolism respiratory, never fermentative, Molecular oxygen is the electron acceptor. Oxidase reaction negative or weak. Catalase positive.

In a weekly buffered medium (see footnote c, Table 1), acid is produced in small amounts from many carbohydrates but not from rhamnose, inulin, adonitol, dulcitol, inositol or salicin and rarely from sorbitol. No acid produced in purple milk. Acetate, citrate, malate, propionate and succinate are utilized but generally not benzoate, oxalate or tartrate; gluconate may be untilised after a delay. Most species hydrolyze starch and Tween 80 rapidly. ("Tween" is a Trade Mark).

Nitrates not reduced. Hydrogen sulfide produced from cysteine and by most species from thiosulfate and peptone. Acetoin and indole not produced, sodium hippurate not hydrolyzed.

Minimal growth requirements are complex and usually include methionine, glutamic acid and nicotinic acid in various combinations. Asparagine not utilized as a sole source of carbon and nitrogen. Growth on nutrient agar inhibited by 0.1% and usually by 0.02% triphenyltetrazolium chloride.

Strict aerobes.

Temperature optimum 25°–27° C.; none grow at 5° C., most grow at 7° C. but some unable to grow below 9° C.; all grow at 30° C., none grow at 40° C.

The G+C content of the DNA of 29 nomen-species of the *X. campestris* group ranges from 63.5–69.2 moles % (mostly $T_m$)."

The various major distinct groups may be distinguished as set out in Table 1.

TABLE 1

| | *X campestris* | *X fragariae* | *X albilineans* | *X axonopodis* | *X ampelina* |
|---|---|---|---|---|---|
| Growth at 35° C. | +[a] | + | + | + | −[a] |
| Hydrolysis of esculin[b] | + | + | + | + | − |
| Mucoid growth on nutrient glucose agar | + | + | − | − | − |
| Gelatin liquefaction | + | + | d | − | − |
| Proteolysis of milk | + | − | − | − | − |
| $H_2S$ from peptone | + | − | − | + | d |
| Urease | − | − | − | − | + |
| Tolerance of NaCl % | 2.0–5.0 | 0.5–1.0 | <0.5 | 1.0 | 1.0 |
| Acid production[c] from: | | | | | |
| Arabinose | + | − | − | − | + |
| Glucose | + | + | + | + | − |
| Mannose | + | + | + | − | − |
| Galactose | + | − | d | − | + |
| Trehalose | + | − | − | + | − |
| Cellobiose | + | − | − | − | − |

[a],+ = 90% or more of strains positive in this character; − = 90% or more of strains negative in this chacacter; d = some (less than 90%) strains positive, some negative.
[b]Some reactions delayed
[c]Within 21 days by the method of Dye, "The inadequacy of the usual determinative tests for the identification of Xanthomonas spp.", New Zealand J. Sci., Vol 5 (1962), pp 393–416.

*Xanthomonas juglandis* is now regarded as a distinct nomenspecies characterized by its hosts specificity (for walnut trees, Juglans spp), but is otherwise characterised as a member of the *X campestris* group.

Despite the above reference to complex growth requirements, and the teaching of McNeely (U.S. Pat. No. 3391060 and Industrial Gums), it has been found by the present inventors that cell growth and high polysaccharide production may be achieved simultaneously when Xanthomonas bacteria are grown in a chemically defined medium in continuous culture.

The culture medium used in the process of the present invention preferably contains a polyhydric alcohol, for example glycerol or a carbohydrate, such as glucose, sucrose, fructose or starch, as its carbon source. For the production of useful yields, a high concentration of carbon source is required and the total concentration of available carbon should be at least 10 gm/liter (calculated as elemental carbon). Higher concentrations, especially between 15 and 24 gms/liter may often be preferred but very high concentration may interfere with the process due to excessive increases in viscosity of the medium.

The nitrogen source is preferably an inorganic salt such as ammonium nitrate or, which is particularly preferred, a salt containing nitrogen in only one of its cation and anion, eg ammonium chloride. However the nitrogen source may also be an amino acid, such as asparagine or, which is preferred, glutamic acid, or an amino acid salt, such as an asparagine salt or which is preferred, a glutamate.

In some cases, a medium containing only a single nitrogen source (ie wherein nitrogen is present as only a single chemical species) is preferred.

Examples of this type of nitrogen source include inorganic salts that contain nitrogen in either the cation or the anion (but not both), and amino acids such as glutamic acid and asparagine.

Preferably, even when it is the growth limiting substrate, the nitrogen source is present in the medium at a concentration of at least 0.7 gm liter$^{-1}$ (calculated as elemental nitrogen).

The sources of phosphorus, sulphur, magnesium, potassium and other elements essential for cell growth are salts such as phosphates, sulphates, halides, oxides, and borates which provide these essential elements in the form of inorganic ions in solution.

It is also important that the present culture medium (the one supplied to the culture vessel) consists of a known ratio of the known chemical ingredients. This is generally achieved by dissolving known amounts of these ingredients in a suitable, generally aqueous, solvent.

The Xanthomonas seed culture may be grown in either a chemically defined or a complex medium. At first sight this may seem slightly anomalous, since it may mean that a complex medium is initially introduced to the culture vessel in the manner of McNeely. However, unlike the batch culture of McNeely (U.S. Pat. No. 3391060) in which complex components are present in the culture vessel throughout the final fermentation, the present continuous process, in which culture medium is continually added to and removed from the culture vessel, ensures that the concentration of complex components in the culture vessel will be reduced to ineffective levels in a short time.

The culture conditions, apart from the culture medium, should be within the conventional ranges used for Xanthomonas culture. The pH of the culture should normally be between 6.0 and 8.0 and preferably between 6.5 and 7.5 for optimum polysaccharide production. The pH may be maintained at this level by controlled addition of base and/or acid using a pH controller. Alternatively or additionally, pH control may be achieved by buffering the culture medium with a conventional buffer such as sodium dihydrogen phosphate, which may also act as a phosphorus source. The temperature is less critical, but will generally be between 20° and 40° C. Temperatures within the range 25° to 35° C. are generally preferred.

As further understood in the art, culture processes in accordance with the present invention will normally be conducted under aerobic conditions achieved by a flow of oxygen or air through the culture medium, generally assisted by stirring. Air flows of about 1 vol air per volume of culture each minute are generally suitable. Oxygen flow rates may, of course, be lower and the use of oxygen may therefore be preferred in very viscous (ie high yielding) media.

Although reasonable polysaccharide production may be achieved using mean residence times of the medium in the culture vessel (volume divided by flow rate=the reciprocal of dilution rate) as low as 9 hours, for high polysaccharide yields the mean residence time should be at least 12 hours. Furthermore when using media with certain limiting nutrilites, such as phosphorus, minimum residence times should be somewhat higher still. Minimum useful mean residence times will generally be about twice the mean residence time at which washout of bacteria is observed with the same bacterial species and culture medium. Optimum mean residence times will be somewhat higher, general 12 to 25 hours. Although longer mean residence times, up to about 100 hours, may be used, these reduce the advantages of continuous over batch cultures and are not preferred.

The Xanthan gum may be separated from the culture by any convenient method known in the art. Alternatively the whole culture may be used with or without previously killing the bacteria, depending on the intended use.

A further advantage of a chemically-defined medium is that it facilitates control of the growth-limiting substrate or nutrilite (also called the limiting nutrient). The rate of cell growth in the culture, in otherwise optimum conditions, will depend on the available concentrations of the elements essential for growth. In practice, these concentrations will never be completely in balance and hence one element, or nutrilite, will be present at a concentration less than proportionate to the others in relation to the requirements of the organism. This element is termed the limiting nutrilite.

The limiting nutrilite may be selected by analysing the elemental composition of the bacterial cells and arranging that elements other than the limiting nutrilite are present in the culture medium in considerably greater proportions than those found in the analysis. That growth is limited by the chosen nitrilite can be confirmed by substantially increasing (eg doubling) its concentration in the medium which should cause an increase in cell concentration. (The design of such chemically defined media was described by Evans, Herbert & Tempest in Methods in Microbiology, Vol. 2, pp 310 ∝ 313, edited by Norris & Ribbons, Academic Press 1970).

It has been found that changes in limiting nutrilite influence both the yield and properties of polysaccharides produced by Xanthomonas bacteria, especially *X. campestris* and *X. juglandis*. Sulphur limitation is preferred, whilst phosphorus and nitrogen limitation also yields good results. Magnesium and potassium limitation may also be used. In a particularly preferred embodiment of the present process the growth limiting substrate is the sulphur source and polysaccharide yield is sustained at at least 1.95% (wt %) for at least 22.7 culture turnovers. In another preferred embodiment the growth limiting substrate is the phosphorus source and the polysaccharide yield is at least 1.75 wt % for at least 34.5 turnovers. In yet another preferred embodiment the growth limiting substrate is the nitrogen source and the polysaccharide yield remains at at least 1.2 wt % for at least 22 culture turnovers.

Specific processes in accordance with the present invention will now be described by way of example. These Xanthomonas strains described are publicly available on application to the appropriate depository, subject to national plant health regulations. A comparison of *X. juglandis* with the strain of *X. campestris* deposited with the American Type culture Collection under ATCC 13951 and commonly used in the production of polysaccharides, indicated the difference shown in Table 2.

TABLE 2

| | *X juglandis* ICPB XJ107 | *X campestris* ATCC 13951 |
|---|---|---|
| fermentation of | | |
| *laevulose* | no acid after 10 days | strong acid after 5 days |
| *inositol* | no acid after 10 days | slight acid after 10 days |
| *rhamnose* | no acid after 10 days | slight acid after 10 days |
| *maltose* | weak acid | strong acid |
| indole production | none | slight |

Crude polysaccharide yield was measured by precipitating total precipitatable material from the culture broth by the addition of three volumes of acetone. Apparent viscosities of culture broths were measured, over a range of shear rates, in a Wells-Brookfield "cone and plate" viscometer, model HBT, at a temperature of 25° C. using the 0.8° cone and 0.5 ml samples. The consistency index—the apparent viscosity at no shear and known as the K value—was determined by extrapolation from a log—log plot of apparent viscosity against shear rate.

Polysaccharide for analysis was obtained by diluting one part of culture broth with nine parts of deionised water and centrifuging at 9,000 g for 90 minutes to remove bacterial cells; the polysaccharide was then reprecipitated with three volumes of acetone. The samples so produced contained no detectable free glucose.

In all of the following examples the experiments were deliberately terminated after the stated period for experimental convenience and not because of contamination or any reduction in yield.

EXAMPLE 1

(Sulphur Limited)

A single colony of *X. juglandis* NCPPB 1659 taken from a 24 hour culture plate (a mixture of a tryptic hydrolysate of casein and an enzymic digest of soya bean metal sold as Tryptone Soya Agar by Oxoid Ltd) was inoculated into a 2 liter conical flank containing 200 ml of a sterile medium composed of 3% Tryptone Soya Broth (Oxoid Ltd), 1% glucose, pH 7.0. This seed culture was incubated with aeration by shaking for 2 days at 30° C. and then transferred to a 2½ liter continuous vessel (similar to that described by Evans, Herbert and Tempest in Methods in Microbiology 2 (1970), see above) containing 2 liters of a culture medium composed of:

| | | mg/liter |
|---|---|---|
| Nitrogen | (added as 5.35 gm $liter^{-1}$ of ammonium chloride) | 1400 |
| Phosphorus | (added as 2.4 gm $liter^{-1}$ of sodium dihydrogen phosphate) | 620 |
| Sulphur | (added as 0.142 gm $liter^{-1}$ of sodium sulphate) | 32 |
| Potassium | (added as 0.381 gm $liter^{-1}$ of potassium chloride) | 200 |
| Magnesium | (added as 0.05 gm $liter^{-1}$ of magnesium oxide) | 30 |

-continued together with 45 gm/liter glucose (18 gm/liter carbon) and traces of various metals such as zinc, copper, cobalt, iron, manganese and molybdenum. Air was supplied at 1 vol air/vol culture/min and the culture was stirred at 1000 rpm. The culture was allowed to grow batchwise for 48 hours at 30° C. and pH 6.8 and then flow of the same medium to give a mean residence time of 22 hours (dilution rate of 0.046 per hour) was started. The culture was maintained at 30° C. and pH 6.8 throughout. Polysaccharide was produced continuously from about the middle of the batch culture period until the experiment was voluntarily terminated after 500 hours (22.7 culture turnovers) in the steady state.

A steady state yield of crude polysaccharide of 19.5 gm/liter as measured by acetone precipitation from the culture broth was reached after about 3 days and maintained to the end of the experience. Culture broth consistency index (K value) was 11,000 cps.

EXAMPLE 2

(Sulphur Limited)

The procedure of Example 1 was repeated except that the *Xanthomonas juglandis* strain was NCPPB 411 and the mean residence time was 26 hours. The crude polysaccharide yield of 10.5 gm/liter was reached after about 3 days and maintained for 215 hours (8.3 turnovers). Culture broth K values not available.

EXAMPLE 3

(Sulphur Limited)

The procedure of Example 1 was repeated except that the *X. juglandis* strain was NCPPB 412 and the mean residence time was 38.5 hours. The yield of crude polysaccharide 14 gm/liter was reached after about 4 days and maintained for 200 hours (5.2 turnovers). Culture broth K values were not less than 5,300 cps.

EXAMPLE 4

(Sulphur Limited)

The procedure of Example 3 was repeated except that the *X. juglandis* strain was NCPPB 413. The crude polysaccharide yield of 19 gm/liter was reached after about 4 days and maintained for 205 hours (5.3 turnovers). Culture broth K values were not less than 5,600 cps.

EXAMPLE 5

(Sulphur Limited)

The procedure of Example 3 was repeated except that the *X. juglandis* strain was NCPPB 414. The crude polysaccharide yield of 17 gm/liter was reached after about 4 days and maintained for 680 hours (17.7 turnovers). Culture broth K values were not less than 9,200 cps.

EXAMPLE 6

(Sulphur Limited)

The procedure of Example 1 was repeated except that the *X. juglandis* strain was NCPPB 415 and the mean residence time was 31 hours. The crude polysaccharide yield of 23 gm/liter was reached after about 3 days, and maintained for 820 hours (26.4 turnovers). Culture broth K values were not less than 7,700 cps.

EXAMPLE 7

(Sulphur Limited)

The procedure of Example 6 was repeated except that the *X. juglandis* strain was NCPPB 1447. The crude polysaccharide yield of 27.5 gm/liter was reached after about 3 days and maintained for 500 hours (16.1 turnovers). Culture broth K value was 15,500 cps.

EXAMPLE 8

(Sulphur Limited)

The procedure of Example 3 was repeated except that the *X. juglandis* strain was NCPPB 362. The yield of crude polysaccharide 33 gm/liter was reached after about 3 days and maintained for 290 hours (7.5 turnovers). Culture broth K values were not less than 4,400 cps.

EXAMPLE 9

(Sulphur Limited)

The procedure of Example 1 was repeated except that the *X. juglandis* strain was ATCC 11324 and the mean residence time 50 hours. The crude polysaccharide yield of 20 gm/liter was reached after about 7 days and maintained for 400 hours (8 turnovers). Culture broth K values were not less than 15,000 cps.

EXAMPLE 10

(Sulphur Limited)

The procedure of Example 1 was repeated except that the *X. juglandis* strain was ICPB XJ107, the content of glucose in the medium was increased to 50 gm/liter and the mean residence time was reduced to 16.5 hours. The crude polysaccharide yield of 29 gm/liter was reached after about 3 days and maintained for 1380 hours (83.6 turnovers). Culture broth K values were not less than 15,000 cps.

EXAMPLE 11

(Sulphur Limited)

The procedure of Example 1 was repeated except that the *X. juglandis* strain was a specially active diastatic colony of NCPPB 1659, the carbon source was 20 gm/liter of starch and the mean residence time was increased to 26 hours. The crude polysaccharide yield of 9 gm/liter was reached after about 3 days and maintained for 380 hours (14.6 turnovers). Culture broth K values are not available.

EXAMPLE 12

(Sulphur Limited)

The procedure of Example 1 was repeated using *X. campestris* strain ATCC 13951 (equivalent to NRRL B-1459) and a mean residence time of 29 hours. THe crude polysaccharide yield of 28.5 gm/liter and K value of 21,000 cps were maintained for 703 hours (24.2 turnovers).

EXAMPLE 13

(Sulphur Limited)

Example 1 was repeated except that *X. juglandis* strain was ICPB XJ107, the sulphur content was reduced to 24 mg/liter, the glucose content was increased to 50 gm/liter and the mean residence time was reduced to 16.5 hours. The results obtained are given in Table 3.

TABLE 3

| AGE (hr) | 572 | 644 | 740 | 812 | 906 | 954 | 1,002 |
|---|---|---|---|---|---|---|---|
| Polysaccharide (g/l) | 25.9 | 30.5 | 29.6 | 25.4 | 28.0 | 25.2 | 24.0 |
| Viscosity (CPS) | 18,000 | 17,500 | 17,000 | 17,000 | 19,500 | 17,500 | 18,000 |
| Glucose used (g/liter) | 41.9 | 44.5 | 44.5 | 44.8 | 43.1 | 41.65 | 41.9 |

EXAMPLE 14

(Phosphorus Limited)

The procedure of Example 1 was repeated with *X. juglandis* ICPB XJ 107, a mean residence time of 43 hours (dilution rate 0.023 hour$^{-1}$) using a phosphorus limiting medium wherein the content of phosphorus was reduced to 62 mg/liter and sulphur increased to 320 mg/liter; the concentration of glucose in the medium was decreased to 40 gm/liter. The crude polysaccharide yield of 17.5 gm/liter was reached after about 5 days and maintained for 1500 hours (34.5 turnovers). Culture broth K values were not less than 5200 cps.

EXAMPLE 15

(Nitrogen Limited)

A single colony of *X. juglandis* ICPB XJ107 taken from a 24 hour culture plate (a mixture of a tryptic hydrolysate of casein and an enzymic digest of soya bean meal sold as Tryptone Soya Agar by Oxoid Ltd) was inoculated into a 2 liter conical flask containing 200 ml of a sterile medium composed of 3% Tryptone Soya Broth (Oxoid Ltd), 1% glucose, pH 7.0. This seed culture was incubated with aeration by shaking for 2 days at 30° C. and then transformed to a 2½ liter continuous culture vessel (similar to that described by Evans, Herbert and Tempest in Methods in Microbiology 2 (1970), see above) containing 2 liters of a culture medium composed of:

| | | mg/liter |
|---|---|---|
| Nitrogen | (added as 2.675 gm $liter^{-1}$ of ammonium chloride) | 700 |
| Phosphorus | (added as 2.4 gm $liter^{-1}$ of sodium dihydrogen phosphate) | 620 |
| Sulphur | (added as 1.42 gm $liter^{-1}$ of sodium sulphate) | 320 |
| Potassium | (added as 0.381 gm $liter^{-1}$ of potassium chloride) | 200 |
| Magnesium | (added as 0.05 gm $liter^{-1}$ of magnesium oxide) | 30 | together with 30 gm/liter glucose (12 gm/liter carbon) and traces of various metals such as zinc, copper, cobalt, iron, maganese and molybdenum. Air was supplied at 1 vol air/vol culture/min and the culture was stirred at 1000 rpm. The culture was allowed to grow batchwise for 48 hours at 30° C. and pH 6.8 and the flow of the same medium to give a mean residence time of 28 hours (dilution rate of 0.036% per hour) was started. The culture was maintained at 30° C. and pH 6.8 throughout. Polysaccharide was produced continuously from about the middle of the batch culture period until the experiment was voluntarily terminated after 640 hours (22 turnovers) in the steady state.

A steady state yield of crude polysaccharide of 12 cm/liter as measured by acetone precipitation from the culture broth was reached after about 3 days and maintained to the end of the experiment. Culture broth consistency index (K value) was not less than 1800 cps.

EXAMPLE 16

(Nitrogen Limited)

The procedure of Example 15 was repeated using a glucose concentration of 50 gm/liter and a dilution rate of 0.33 per hour. The composition of the effluent culture broth and the glucose actually consumed at various states in the culture is shown in Table 4.

TABLE 4

| AGE (hr) | 191 | 239 | 359 | 479 | 551 | 839 |
|---|---|---|---|---|---|---|
| Polysaccharide (gm/liter) | 23.0 | 23.0 | 22.0 | 21.0 | 24.5 | 23.3 |
| Viscosity (CPS) | 14,750 | 14,000 | 14,500 | 15,000 | 15,000 | 14,500 |
| Glucose Used (gm/liter) | 36.9 | 39.1 | 34.7 | 35.1 | 36.1 | 37.5 |

EXAMPLES 17a AND b (Nitrogen Limited)

*X. campestris* strain ATCC13951 was grown in the nitrogen limited medium of Example 15 with glucose content increased to 60 g/l. The dilution rate was held at 0.042 for 786 hours (Example 17a) after which it was increased to 0.059 for a further 1496 hours (Example 17b) after which the culture was deliberately terminated with the polysaccharide yield still at 27.1 gm/liter and the viscosity at 34,000 cps. Thus the yield was sustained in the simple salts medium for nearly 2300 hours (Q=121.3). Full results are shown in Table 5.

TABLE 5

| AGE (hr) | 258 | 402 | 786 | 1074 | 1456 | 2177 | 2296 |
|---|---|---|---|---|---|---|---|
| Dilution rate (hr$^{-1}$) | 0.042 | 0.042 | 0.042 | 0.059 | 0.059 | 0.059 | 0.059 |
| Polysaccharide gm/liter | 28.5 | 31.5 | 29.3 | 26.7 | 28.8 | 26.5 | 27.1 |
| Viscosity (CPS) | 19,000 | 24,500 | 22,000 | 30,000 | 32,000 | 36,000 | 34,000 |

EXAMPLES 18a AND b (Nitrogen Limited)

Example 17 was repeated except that the ammonium chloride in the nitrogen limited defined medium was replaced by ammonium nitrate in a quantity to give the same total nitrogen content. The dilution rates were 0.045 hr$^{-1}$ and 0.06 hr$^{-1}$. Results are shown in Table 6.

TABLE 6

| AGE hr | 258 | 402 | 570 | 834 | 1170 | 1456 | 2008 |
|---|---|---|---|---|---|---|---|
| Dilution rate (hr$^{-1}$) | 0.045 | 0.045 | 0.045 | 0.06 | 0.06 | 0.06 | 0.06 |
| Polysaccharide (gm/liter) | 28.5 | 29.1 | 29.5 | 33.4 | 31.9 | 30.9 | 30.06 |
| Viscosity (CPS) | 20,000 | 22,000 | 22,500 | 36,500 | 36,000 | 36,000 | 39,000 |

EXAMPLE 19a, b AND c (Nitrogen Limited)

Example 17 was repeated except that the ammonium chloride in the medium was replaced by an equivalent amount (9.35 gm/liter) of glutamate as sodium glutamate. The dilution rate was 0.033 for the first 259 hours (Example 19a). When it became apparent that the culture was growing successfully this was increased to 0.05 for 151 hours (Example 19b) and then to 0.06 for the remainder of the experiment (Example 19c). Results are shown in Table 7.

TABLE 7

| AGE hr | 162 | 258 | 402 | 426 | 498 | 594 |
|---|---|---|---|---|---|---|
| Dilution rate (hr$^{-1}$) | 0.033 | 0.033 | 0.05 | 0.06 | 0.06 | 0.06 |
| Polysaccharide (gm/liter) | 30.6 | 30.7 | 28.7 | 30.8 | 31.7 | 35.0 |
| Viscosity (CPS) | 34,000 | 30,000 | 27,000 | 28,500 | 28,500 | 38,500 |

EXAMPLE 20a–e (Nitrogen Limited)

The continuous culture of Example 19 was allowed to continue for a further 1434 hr. During that time the dilution rate was varied between 0.06 and 0.107 is between mean residence times of 17 and 9.3 hr). Results are shown in Table 8.

TABLE 8

| Age (hr) | 1096 | 1332 | 1500 | 1596 | 2028 |
|---|---|---|---|---|---|
| Dilution Rate (hr$^{-1}$) | 0.06 | 0.08 | 0.09 | 0.107 | 0.10 |
| Polysaccharide (gm/liter) | 36.0 | 34.2 | 31.6 | 26.9 | 29.8 |
| Viscosity (cps) | 36,000 | 31,000 | 31,500 | 24,500 | 26,000 |

EXAMPLE 21

(Potassium Limited)

The procedure of Example 1 was repeated with *X. juglandis* ICPB XJ107, the mean residence time adjusted to 33 hours (dilution rate 0.03 hour$^{-1}$), the potassium content of the medium reduced to 40 mg/liter, the sulphur content increased to 320 mg/liter, to give potassium-limited conditions, and the glucose concentration decreased to 30 gm/liter. The crude polysaccharide yield of 9 gm/liter was reached after about 6 days and maintained for 2060 hours (61.8 turnovers). Culture broth K values were 360 cps.

EXAMPLE 22

(Magnesium Limited)

The procedure of Example 1 was repeated using *X. juglandis* strain ICPB XJ107, a magnesium limiting medium wherein the content of magnesium was reduced to 6 mg/liter, the sulphur content was increased to 320 mg/liter the glucose concentration was decreased to 30 gm/liter and the mean residence time was increased to 33 hrs. The crude polysaccharide yield of 9 gm/liter was reached after about 4 days and maintained for 280 hours, (8.4 turnovers). No culture broth K values are available.

COMPARATIVE EXAMPLES

EXAMPLE 23

(Batch process)

*X. juglandis* strain ICPB XJ107 was grown in batch culture in the medium of Example 15 with the glucose concentration increased to 45 gm/liter. After 69 hours the yield of polysaccharide was 13.5 gm/liter (K value 2,600); after 93 hours and the disappearance of all the glucose, the yield was 20.5 gm/liter and the K value of the culture broth was 15,000 cps.

EXAMPLE 24

(Batch process)

*X. campestris* strain ATOC 13951 was grown in batch culture in the medium of Example 1. After 117 hrs the yield of crude polysaccharide was 28 gm/liter and the K value of the culture broth was 18,000 cps.

EXAMPLE 25

(Nitrogen Limited)

An experiment using a nitrogen limiting "complex" culture medium with *X. juglandis* was also carried out using conditions similar to those described in Example 16, but with a culture medium consisting of:

|  | gm/liter |
|---|---|
| Malt extract | 3.0 |
| Yeast extract | 3.0 |
| Mycological peptone | 5.0 |
| Pot.dihydrogen phosphate | 2.0 |
| Glucose | 50.0 |
| pH | 7.0 | and a dilution rate of 0.0325 per hour.

The results obtained are shown in Table 9 from which it can be seen that the yield fell-off progressively from about 225 hours (7.3 turnovers) onwards. It is emphasised that apart from the culture medium (and a slightly lower dilution rate) the conditions were, within experimental error, identical to those used in Example 16 (c.f. Table 4).

TABLE 9

| AGE (hr) | 215 | 239 | 311 | 359 | 407 |
|---|---|---|---|---|---|
| Polysaccharide (gm/liter) | 22.6 | 18.0 | 17.7 | 13.5 | 10.0 |
| Viscosity (CPS) | 11,500 | 8,000 | 6,400 | 3,900 | 2,350 |
| Glucose used (gm/liter) | 37.4 | 33.4 | 24.8 | 22.6 | 10.8 |

EXAMPLE 26

(Nitrogen Limited-Complex medium)

Example 25 was repeated using *X. campestris* strain ATCC 13951, a glucose concentration of 60 gm/liter and dilution rate of 0.033 hr$^{-1}$. The initial yield was very high and was maintained for an exceptionally long time, for a culture grown in complex medium, (400–500 hours; culture turnovers (Q)=13–17). However even this optimised culture eventually showed a fall-off in yield after 500–650 hours (Q=17–21) with the viscosity falling from 22,000 to 1,300 centi-poise. Full results are shown in Table 10.

TABLE 10

| AGE (hr.) | 240 | 336 | 504 | 576 | 648 |
|---|---|---|---|---|---|
| Polysaccharide (gm/liter) | 33.8 | 34.5 | 26.3 | 19.5 | 12.1 |
| Viscosity (CPS) | 20,500 | 22,200 | 17,500 | 10,000 | 1,300 |

This experiment should be compared with Example 17a and b, illustrating the present invention. In Example 17 the polysaccharide yield was sustained in a simple salts medium for nearly 2300 hr (Q=122) whereas in the complex medium of Example 26 the yield could be maintained for no more than 500 hr (Q=16.5).

EXAMPLE 27

(Nitrogen Limited)

In this experiment the batch culture of Example 1 of U.S. Pat. No. 3,391,060 (McNeely) was repeated except that the final fermentation stage of that Example was conducted on a continuous rather than a batch basis and the amounts employed were reduced on a pro rata basis. A stock culture of *Xanthomonas campestris* ATCC 13951 was grown on a potato dextrose agar slant. From the potato dextrose slant a transfer was made to a sterile YM agar slant. From the YM agar slant a transfer was made into 100 ml of 2.1% YM broth in a 500 ml Erlenmeyer flask. After 24 hr of incubation at 20° C. under aerobic conditions, 15 ml of the culture were transferred aseptically into 200 ml of sterile 2.1% YM broth in a one liter flask. This flask was incubated for 24 hr under aerobic conditions at 30° C. 15 ml of the culture were then transferred aseptically into a one liter flask containing 200 ml of a sterile medium (medium A) having the following composition:

Ammonium nitrate (0.045%)
Soy Peptone Type T (0.3%)
Dipotassium hydrogen phosphate (0.5%)
Magnesium sulphate heptahydrate (0.01%)
Glucose (2%)
Water to make 200 ml The fermentor was maintained at 30° C. for 24 hr under aeration and agitation to give a sulphite oxidation value in the range of 2.0 to 3.0 mmoles of oxygen per liter of medium per minute.

15 ml of the culture were transferred aseptically into a 2.5 liter fermentor containing 2 liters of sterile medium A (except that, in the manner of U.S. Pat. No. 3,391,060 the glucose concentration had been reduced to 1.3%).

The fermentor was maintained at 30° C. for 24 hr under aeration and agitation to give a sulphite oxidation value in the range of 2.0 to 3.0 mmoles of oxygen per liter of medium per minute.

93 ml of the culture were then transferred aseptically into a 2.5 liter fermentor containing 2 liters of a sterile medium (medium B). Medium B had the following composition:
Ammonium nitrate (0.06%)
Dipotassium hydrogen phosphate (0.5%)
Magnesium sulphate heptahydrate (0.01%)
Glucose (2.25%)
Water (97.18%)

The fermentor was maintained at a temperature of 30° C. for 72 hr under a combination of aeration and agitation to give a sulphite oxidation value in the range of 2.0 to 3.0 mmoles of oxygen per liter of medium per minute. At the end of the 72 hr the fermentation beer had an apparent viscosity of 16,000 cps (K value) as measured by the Wells Brookfield 0°-8° cone (0.5 ml sample at 25° C.); equivalent to 3000 cps as measured by the method of McNeely. The colloid content of the beer was 1.6% and the sugar content was 0.04%.

After this time the fermentor was switched to the continuous mode. Medium B was added to the fermentor and the vessel contents were withdrawn from the fermentor to give a mean residence time in the culture vessel of 30 hr. (This rather long residence time was chosen to give the system the maximum chance of success).

After 47 hr onflow the viscosity of the beer had fallen to a K value of 4,400 cps. After 213 hr on flow the viscosity of the beer had fallen to a K value of 3000 cps (viscosity as measured by the method of McNeely of 575 cps) and the polysaccharide yield was 1%.

EXAMPLE 28

The process of Example 27 was allowed to continue except that aftr 218 hr on flow the culture medium was changed to a medium having the composition of the medium described in Example 17. After 43 hr growth in this medium, the viscosity of the culture had risen to a K value of 10,000 cps. After a further 44 hr growth, the viscosity had risen to 30,000 cps. At a total culture age of 478 hr the present medium was diluted to a glucose concentration of 22.5 gm/l to enable comparison to be made with the medium of McNeely. After 47 hr growth in this medium, the viscosity, measured as K values, was 9,000 cps. The viscosity remained at this level until the culture was deliberately terminated.

The results achieved in Examples 1 to 27 are summarised in Table 11 whilst Table 12 shows chemical analyses of some purified cell free materials. It is emphasised that none of the chemically defined media (other than that of McNeely, Example 27) showed the characteristic fall in yield shown in comparative Examples 25 and 26. All other continuous cultures, run according to the present invention, were deliberately terminated at the ages shown without significant fall in yield having occurred.

TABLE 11

| Example | Strain | Limiting Element | Steady State Duration (Hr) | Mean Residence Time (Hr) | Culture Turnovers (Q) | Carbon Source | Amount of Carbon Source Used (Gm/Liter) | Culture K value (cps) | Crude Polysaccharide Yield (Gm/Liter) |
|---|---|---|---|---|---|---|---|---|---|
| 1 | NCPPB 1659 | Sulphur | 500 | 22 | 22.7 | Glucose | 27 | 11,000 | 19.5 |
| 2 | NCPPB 411 | S | 215 | 26 | 8.3 | Glucose | 42.5 | NA | 10.5 |
| 3 | NCPPB 412 | S | 200 | 38.5 | 5.2 | Glucose | 44.5 | 5,300 | 14 |
| 4 | NCPPB 413 | S | 205 | 38.5 | 5.3 | Glucose | 44.5 | 5,600 | 19 |
| 5 | NCPPB 414 | S | 680 | 38.5 | 17.7 | Glucose | 35.5 | 9,200 | 17 |
| 6 | NCPPB 415 | S | 820 | 31 | 26.4 | Glucose | 37 | 7,700 | 23 |
| 7 | NCPPB 1447 | S | 500 | 31 | 16.1 | Glucose | 45 | 15,500 | 27.5 |
| 8 | NCPPB 362 | S | 290 | 38.5 | 7.5 | Glucose | 45 | 4,400 | 33 |
| 9 | ATCC 11329 | S | 400 | 50 | 8.0 | Glucose | 44 | 15,000 | 20 |
| 10 | ICPB XJ107 | S | 1380 | 16.5 | 83.6 | Glucose | 38 | 15,000 | 29 |
| 11 | NCPPB 1659 | S | 380 | 26 | 14.6 | Starch | 20 | NA | 9 |
| 12 | ATCC 13951 | S | 703 | 29 | 24.2 | Glucose | 45 | 21,000 | 28.5 |
| 13 | ICPB XJ107 | S | 1002 | 16.5 | 60.7 | Glucose | 41.9 | 18,000 | 24.0 |
| 14 | ICPB XJ107 | P | 1500 | 43 | 34.5 | Glucose | 35 | 5,200 | 17.5 |
| 15 | ICPB XJ107 | N | 640 | 28 | 22.0 | Glucose | 22 | 1,800 | 12 |
| 16 | ICPB XJ107 | N | 839 | 30 | 28.0 | Glucose | 37.5 | 14,500 | 23.3 |
| 17a | ATCC 13951 | N | 786 | 24 | 33.0 | Glucose | NA | 22,000 | 29.3 |
| 17b | | | 1496 | 17 | 88.3 | | | 34,000 | 27.1 |
| 18a | ATCC | N | 570 | 22 | 25.6 | Glucose | NA | 22,500 | 29.5 |

TABLE 11-continued

| Example | Strain | Limiting Element | Steady State Duration (Hr) | Mean Residence Time (Hr) | Culture Turnovers (Q) | Carbon Source | Amount of Carbon Source Used (Gm/Liter) | Culture K value (cps) | Crude Polysaccharide Yield (Gm/Liter) |
|---|---|---|---|---|---|---|---|---|---|
| 18b | 13951 | | 1208 | 17 | 72.5 | | | 39,000 | 30.6 |
| 19a | ATCC | N | 259 | 30 | 8.5 | Glucose | NA | 30,000 | 30.7 |
| 19b | 13951 | | 151 | 20 | 7.6 | | | 28,000 | 28.7 |
| 19c | | | 184 | 17 | 11.0 | | | 38,500 | 35.0 |
| 20a | ATCC | N | 1096 | 17 | 56.6 | Glucose | NA | 36,000 | 36.0 |
| 20b | 13951 | | 1332 | 12.5 | 26.9 | | | 31,000 | 34.0 |
| 20c | | | 1500 | 11 | 15.3 | | | 31,500 | 31.6 |
| 20d | | | 1596 | 9.5 | 10.1 | | | 24,500 | 26.9 |
| 20e | | | 2028 | 10 | 43.2 | | | 26,000 | 29.8 |
| 21 | ICPB XJ107 | K | 2060 | 33 | 61.8 | Glucose | 15 | 360 | 9 |
| 22 | ICPB XJ107 | Mg | 280 | 33 | 8.4 | Glucose | 16 | NA | 9 |
| 23 | ICPB XJ107 | "N" | Batch | 69 | — | Glucose | 36.4 | 2,600 | 13.5 |
| | | | | 93 | — | | 45 | 15,000 | 20.5 |
| 24 | ATCC 13951 | "S" | Batch | 117 | — | Glucose | 45 | 18,000 | 28 |
| 25 | ACPB XJ107 | Complex | 215 | 31 | 6.9 | Glucose | 37.4 | 11,500 | 22.6 |
| | | | 311 | 31 | 10.0 | | 24.8 | 6,400 | 17.7 |
| | | | 407 | 31 | 13.1 | | 10.8 | 2,350 | 10.0 |
| 26 | ATCC 13951 | Complex "N" | 336 | 30 | 11.1 | Glucose | NA | 22,200 | 34.5 |
| | | | 504 | 30 | 16.6 | | | 17,500 | 26.3 |
| | | | 576 | 30 | 19.2 | | | 10,000 | 19.5 |
| | | | 648 | 30 | 21.4 | | | 1,300 | 12.1 |
| 27 | ATCC 13951 | N | Batch | 72 | — | Glucose | 0.04 | 16,000 | 1.6 |
| | | | 47 | 30 | 0.8 | | NA | 4,400 | NA |
| | | | 213 | 30 | 7.1 | | NA | 3,000 | 1.0 |

TABLE 12

| Example | Strain | Limiting Element | Analysis (% Carbohydrate Detected) Rhamnose | Mannose | Glucose | Glucose/Mannose Ratio |
|---|---|---|---|---|---|---|
| 1 | NCPBB 1659 | S | 4.2 | 32.0 | 64.0 | 1.98 |
| 2 | NCPPB 411 | S | 22.95 | 26.1 | 46.4 | 1.78 |
| 3 | NCPPB 412 | S | 12.6 | 38.1 | 44.3 | 1.16 |
| 4 | NCPPB 413 | S | 9.5 | 36.6 | 46.0 | 1.26 |
| 5 | NCPPB 414 | S | 3.6 | 41.5 | 58.4 | 1.41 |
| 6 | NCPBB 415 | S | 6.0 | 45.0 | 46.8 | 1.04 |
| 7 | NCPPB 1447 | S | 7.0 | 43.0 | 49.0 | 1.14 |
| 8 | NCPPB 362 | S | 10.4 | 41.5 | 46.0 | 1.12 |
| 9 | ATCC 11329 | S | 11.0 | 32.6 | 39.1 | 1.20 |
| 10 | ICPB XJ107 | S | 11.2 | 38.2 | 48.0 | 1.26 |
| 11 | NCPPB 1659 | S | 14.0 | 25.0 | 49.0 | 1.95 |
| 14 | ICPB XJ107 | P | 3.0 | 46.8 | 48.9 | 1.05 |
| 15 | ICPB XJ107 | N | 11.2 | 38.0 | 49.0 | 1.29 |
| 22 | ICPB XJ107 | Mg | 7.0 | 43.9 | 47.4 | 1.08 |
| 23 | ICPB XJ107 | "N" | 5.5 | 47.9 | 46.6 | 0.97 |

EXAMPLE 29

(Nitrogen Limited)

Example 17 was repeated except that the ammonium chloride in the medium was replaced by an equivalent amount (9.35 gm/liter) of glutamate as sodium glutamate. The dilution rate was maintained at 0.066 throughout the experiment to examine the stability of the culture in this medium. The results of this experiment, which was deliberately terminated at 790 hr, are shown in Table 13.

TABLE 13

| Age (hr) | 115 | 259 | 331 | 499 | 619 | 787 |
|---|---|---|---|---|---|---|
| Dilution Rate (hr$^{-1}$) | 0.065 | 0.066 | 0.066 | 0.066 | 0.066 | 0.066 |
| Polysaccharide (gm/liter) | 28.2 | 29.2 | 29.5 | 29.6 | 26.0 | 27.8 |

TABLE 13-continued

| Age (hr) | 115 | 259 | 331 | 499 | 619 | 787 |
|---|---|---|---|---|---|---|
| Viscosity (CPS) | 18,500 | 20,000 | 22,500 | 21,500 | 21,500 | 21,500 |

EXAMPLE 30

(Nitrogen Limited)

The procedure of Example 29 was repeated except that the sodium glutamate was replaced by an equivalent amount (3.3 gm/liter) of asparagine. The dilution rate was 0.042 $hr^{-1}$ for the first 598 hr after which it was increased to 0.062 $hr^{-1}$ for the remainder of the experiment. The results are shown in Table 14.

TABLE 14

| Age (hr) | 190 | 310 | 478 | 598 | 646 | 694 |
|---|---|---|---|---|---|---|
| Dilution Rate ($hr^{-1}$) | 0.042 | 0.042 | 0.042 | 0.042 | 0.062 | 0.062 |
| Polysaccharide (gm/liter) | 25.9 | 28.0 | 28.6 | 29.5 | 28.3 | 28.6 |
| Viscosity (CPS) | 18,500 | 18,000 | 28,500 | 30,000 | 26,500 | 26,500 |

EXAMPLE 31

(Nitrogen limited)

Example 17 was repeated except that the ammonium chloride was replaced by an equivalent amount of ammonium nitrate. The dilution rate varied between 0.051 and 0.086 $hr^{-1}$. The results are shown in Table 15.

TABLE 15

| Age (hr) | 138 | 330 | 402 | 546 | 666 | 738 | 856 | 1072 | 1193 |
|---|---|---|---|---|---|---|---|---|---|
| Dilution rate ($hr^{-1}$) | 0.051 | 0.057 | 0.065 | 0.065 | 0.073 | 0.073 | 0.078 | 0.083 | 0.086 |
| Polysaccharide (gm/liter) | 29.7 | 29.2 | 28.2 | 27.9 | 26.9 | 27.4 | 26.5 | 27.3 | 26.0 |
| Viscosity (CPS) | 28,500 | 33,000 | 32,000 | 30,000 | 27,000 | 27,000 | 27,500 | 28,000 | 27,000 |

We claim:

1. A process for the production of a polysaccharide by culturing polysaccharide-producing bacteria of the *Xanthomonas campestris* group in continuous culture, comprising:
   (a) introducing into a culture vessel a culture of polysaccharide-producing bacteria of the *Xanthomonas campestris* group;
   (b) continuously supplying a culture medium to the culture vessel at a rate such that an essentially steady state is maintained in the vessel;
   (c) maintaining conditions of aeration, pH and temperature within the culture vessel, such as to promote the simultaneous growth of bacteria and production of polysaccharides; and
   (d) continuously withdrawing the resulting polysaccharide-containing culture broth from the culture vessel at substantially the same rate as the culture medium is supplied to the culture vessel, the said culture medium being a chemically-defined culture medium consisting of the following nutrient sources: a carbon source at a concentration of at least 10 gm $liter^{-1}$ calculated as elemental carbon, a nitrogen source, and sources of further elements, consisting of phosphorus, sulphur, magnesium, potassium and elements other than O, H, C, N, P, S, Mg and K, which are essential for the growth of said polysaccharide-producing bacteria, the sources of said further elements being salts that provide said further elements in the form of inorganic ions in solution;
   the medium having a growth-limiting substrate selected from the nitrogen, phosphorus, sulphur, magnesium and potassium source;
   and the nutrient sources, the rate of supply of the culture medium to the culture vessel and the conditions within the culture vessel being selected such that the formation of non-polysaccharide-producing strains of Xanthomonas is substantially reduced and thereby a fall-off in polysaccharide yield is substantially avoided.

2. A process according to claim 1, wherein the bacteria are of the *Xanthomonas juglandis* species.

3. A process according to claim 1, wherein the nitrogen source is an inorganic salt.

4. A process according to claim 3, wherein the growth-limiting substrate is the sulphur source.

5. A process according to claim 4, wherein the nutrient sources, the rate of supply of the culture medium to the culture vessel, and the conditions within the culture vessel are selected such that the polysaccharide yield is at least 1.95 wt % for at least 22.7 culture turnovers.

6. A process according to claim 3, wherein the growth-limiting substrate is the phosphorus source.

7. A process according to claim 6, wherein the nutrient sources, the rate of supply of the culture medium to the culture vessel, and the conditions within the culture vessel are selected such that the polysaccharide yield is at least 1.75 wt % for at least 34.5 culture turnovers.

8. A process according to claim 3, wherein the nitrogen source is an inorganic salt containing nitrogen in only one of its cation and anion.

9. A process according to claim 8, wherein the nitrogen source is ammonium chloride.

10. A process according to claim 3, wherein the growth limiting substrate is selected from the magnesium and potassium sources.

11. A process according to claim 1, wherein the growth-limiting substrate is the nitrogen source.

12. A process according to claim 11, wherein the nutrient sources, the rate of supply of the culture medium to the culture vessel, and the conditions within the culture vessel are selected such that the polysaccharide yield is at least 1.2 wt % for at least 22 culture turnovers.

13. A process according to claim 11, wherein the nitrogen source is an amino acid or an amino acid salt.

14. A process according to claim 13, wherein the nitrogen source is glutamic acid or a glutamate.

15. A process according to claim 13, wherein the nitrogen source is asparagine or an asparagine salt.

16. A process according to claim 1, wherein the culture medium has a mean residence time, of culture medium in the culture vessel, of at least 12 hours.

17. A process according to claim 1, wherein the total concentration of the nitrogen source in the culture medium is at least 0.7 gm liter$^{-1}$, calculated as elemental nitrogen.

18. A process according to claim 11, wherein the carbon source is selected from the group consisting of glycerol and a carbohydrate.

19. A process according to claim 1, wherein the total concentration of the carbon source in the culture medium is between 10 and 24 gm liter$^{-1}$, calculated as elemental carbon.

20. A process for the production of a polysaccharide by culturing polysaccharide-producing bacteria of the *Xanthomonas campestris* group in continuous culture comprising:
  (a) introducing into a culture vessel a culture of polysaccharide-producing bacteria of the Xanthomonas campestris group;
  (b) continuously supplying a culture medium to the culture vessel at a rate such that an essentially steady state is maintained in the vessel;
  (c) maintaining conditions of aeration, pH and temperature within the culture vessel to promote the simultaneous growth of bacteria and production of polysaccharide; and
  (d) continuously withdrawing the resulting polysaccharide-containing culture broth from the culture vessel at substantially the same rate as the culture medium is supplied to the culture vessel;

the said culture medium being a chemically-defined culture medium consisting of the following nutrient sources: a carbon source at a concentration of at least 10 gm liter$^{-1}$ calculated as elemental carbon, a nitrogen source which is an inorganic salt at a concentration of at least 0.7 gm liter$^{-1}$ calculated as elemental nitrogen, and sources of further elements, consisting of phosphorus, sulphur, magnesium, potassium, and elements other than O, H, C, N, P, S, Mg and K, which are essential for the growth of said polysaccharide-producing bacteria, the sources of said further elements being salts that provide said further elements in the form of inorganic ions in solution;

the medium having a growth-limiting substrate selected from the nitrogen, phosphorus, sulphur, magnesium and potassium source; and the nutrient sources, the rate of supply of the culture medium to the culture vessel and the conditions within the culture vessel being selected such that the formation of non-polysaccharide-producing strains of *Xanthomonas campestris* is substantially reduced and thereby a fall-off in polysaccharide yield is substantially avoided.

21. A process for the production of a polysaccharide by culturing polysaccharide-producing bacteria of the *Xanthomonas campestris* group in continuous culture, comprising:
  (a) introducing into a culture vessel a culture of polysaccharide-producing bacteria of the *Xanthomonas campestris* group;
  (b) continuously supplying a culture medium to the culture vessel at a rate such that an essentially steady state is maintained in the vessel;
  (c) maintaining conditions of aeration, pH and temperature within the culture vessel to promote the simultaneous growth of bacteria and production of polysaccharide; and
  (d) continuously withdrawing the resulting polysaccharide-containing culture broth from the culture vessel at substantially the same rate as the culture medium is supplied to the culture vessel, said rate being adjusted to give a mean residence time, of culture medium in the culture vessel, of at least 12 hours;

the said culture medium being a chemically-defined culture medium consisting of the following nutrient sources: a carbon source at a concentration of at least 10 gm liter$^{-1}$ calculated as elemental carbon, a nitrogen source which is ammonium chloride at a concentration of at least 0.7 gm liter$^{-1}$ calculated as elemental nitrogen, and sources of further elements, consisting of phosphorus, sulphur, magnesium, potassium and elements other than O, H, C, N, P, S, Mg and K, which are essential for the growth of said polysaccharide-producing bacteria, the sources of said further elements being salts that provide said further elements in the form of inorganic ions in solution;

the medium having a growth-limiting substrate which is the sulphur source;

and the nutrient sources, the rate of supply of the culture medium to the culture vessel, and the conditions within the culture vessel being selected such that the formation of non-polysaccharide-producing strains of *Xanthomonas campestris* is substantially reduced and thereby a fall-off in polysaccharide yield is substantially avoided.

22. A process for the production of a polysaccharide by culturing polysaccharide-producing bacteria of the *Xanthomonas campestris* group in continuous culture, comprising:
  (a) introducing into a culture vessel a culture of polysaccharide-producing bacteria of the *Xanthomonas campestris* group;
  (b) continuously supplying a culture medium at a rate such that an essentially steady state is maintained in the vessel;
  (c) maintaining conditions of aeration, pH and temperature within the culture vessel to promote the simultaneous growth of bacteria and production of polysaccharide; and
  (d) continuously withdrawing the resulting polysaccharide-containing culture broth from the culture vessel at substantially the same rate as the culture medium is supplied to the culture vessel;

the said culture medium being a chemically-defined culture medium consisting of the following nutrient sources: a carbon source at a concentration of at least 10 gm liter$^{-1}$ calculated as elemental carbon, a nitrogen source, selected from the class consisting of glutamic acid and a glutamate, at a concentration of at least 0.7 gm liter$^{-1}$ calculated as elemental nitrogen, and sources of further elements, consisting of phosphorus, sulphur, magnesium, potassium and elements other than O, H, C, N, P, S, Mg and K, which are essential for the growth of said polysaccharide-producing bacteria, the sources of said further elements being salts that provide said further elements in the form of inorganic ions in solution;

the medium having a growth-limiting substrate which is the nitrogen source;

and the nutrient sources, the rate of supply of the culture medium to the culture vessel, and the conditions within the culture vessel being selected such that the formation of non-polysaccharide-producing strains of *Xanthomonas campestris* is substantially reduced and thereby a fall-off in polysaccharide yield is substantially avoided.

23. A process for the production of a polysaccharide by culturing polysaccharide-producing bacteria of the *Xanthomonas campestris* group in continuous culture, comprising:

(a) introducing into a culture vessel a culture of polysaccharide-producing bacteria of the *Xanthomonas campestris* group;

(b) continuously supplying a culture medium, at a rate such that an essentially steady state is maintained in the vessel;

(c) maintaining conditions of aeration, pH and temperature within the culture vessel to promote the simultaneous growth of bacteria and production of polysaccharide; and (d) continuously withdrawing the resulting polysaccharide-containing culture broth from the culture vessel at substantially the same rate as the culture medium is supplied to the culture vessel;

the said culture medium being a chemically-defined culture medium consisting of the following nutrient sources: a carbon source at a concentration of at least 10 gm liter$^{-1}$ calculated as elemental carbon, a nitrogen source, selected from the class consisting of asparagine and an asparagine salt, at a concentration of at least 0.7 gm liter$^{-1}$ calculated as elemental nitrogen, and sources of further elements, consisting of phosphorus, sulphur, magnesium, potassium and elements other than O, H, C, N, P, S, Mg and K which are essential for the growth of said polysaccharide-producing bacteria, the sources of said further elements being salts that provide said further elements in the form of inorganic ions in solution;

the medium having a growth-limiting substrate which is the nitrogen source;

and the nutrient sources, the rate of supply of the culture medium to the culture vessel, and the conditions within the culture vessel being selected such that the formation of non-polysaccharide-producing strains of *Xanthomonas campestris* is substantially reduced and thereby a fall-off in polysaccharide yield is substantially avoided.

* * * * *